(12) United States Patent
Ruebben

(10) Patent No.: US 10,994,053 B2
(45) Date of Patent: *May 4, 2021

(54) COATING OF A VASCULAR ENDOPROSTHESIS

(71) Applicants: Alexander Ruebben, Monaco (MC); Aachen Scientific International PTE. LTD., Singapore (SG)

(72) Inventor: Alexander Ruebben, Monaco (MC)

(73) Assignees: AACHEN SCIENTIFIC INTERNATIONAL PTE. LTD., Singapore (SG); Alexander Rübben, Monaco (MC)

( * ) Notice: Subject to any disclaimer, the term of this patent is extended or adjusted under 35 U.S.C. 154(b) by 0 days.

This patent is subject to a terminal disclaimer.

(21) Appl. No.: 15/793,275

(22) Filed: Oct. 25, 2017

(65) Prior Publication Data

US 2018/0043060 A1 Feb. 15, 2018

Related U.S. Application Data

(62) Division of application No. 15/021,183, filed as application No. PCT/EP2014/069030 on Sep. 8, 2014, now Pat. No. 9,808,559.

(30) Foreign Application Priority Data

Sep. 10, 2013 (DE) .......................... 102013014821.9

(51) Int. Cl.
| | | |
|---|---|---|
| B05D 3/12 | (2006.01) | |
| A61L 27/54 | (2006.01) | |
| A61L 31/10 | (2006.01) | |
| C09D 105/02 | (2006.01) | |
| A61L 27/34 | (2006.01) | |
| B05D 1/00 | (2006.01) | |

(52) U.S. Cl.
CPC ............... *A61L 27/54* (2013.01); *A61L 27/34* (2013.01); *A61L 31/10* (2013.01); *B05D 1/002* (2013.01); *C09D 105/02* (2013.01); *A61L 2300/606* (2013.01); *A61L 2300/608* (2013.01); *A61L 2420/02* (2013.01); *A61L 2420/08* (2013.01)

(58) Field of Classification Search
USPC ...... 427/2.24, 2.28, 346, 369; 623/1.15–1.48
See application file for complete search history.

(56) References Cited

U.S. PATENT DOCUMENTS

| | | | | |
|---|---|---|---|---|
| 5,464,650 A | * | 11/1995 | Berg .......................... | A61F 2/82 427/2.25 |
| 7,163,715 B1 | | 1/2007 | Kramer | |
| 7,867,547 B2 | * | 1/2011 | Tochterman ............ | B05B 13/02 118/502 |
| 2003/0135255 A1 | | 7/2003 | Sundar | |
| 2005/0015142 A1 | | 1/2005 | Austin et al. | |
| 2007/0275175 A1 | | 11/2007 | Hossainy | |
| 2008/0234812 A1 | * | 9/2008 | Pacetti .................... | B05D 1/002 623/1.46 |
| 2012/0231037 A1 | * | 9/2012 | Levi ........................ | A61L 31/08 424/400 |
| 2013/0345629 A1 | * | 12/2013 | Rubben .................. | A61L 29/08 604/103.02 |

FOREIGN PATENT DOCUMENTS

| | | |
|---|---|---|
| JP | 2011518582 A | 6/2011 |
| WO | 2008/131131 A1 | 10/2008 |
| WO | 2009/059625 A1 | 5/2009 |

OTHER PUBLICATIONS

RD434009A. May 20, 2000 (Year: 2000).*
International Search Report of the International Searching Authority with English translation issued in the corresponding PCT International Application No. PCT/EP2014/069030, dated Dec. 9, 2014 (5 pages).
Written Opinion of the International Search Authority (Form PCT/ISA/237) with English translation issued in the corresponding PCT International Application No. PCT/EP2014/069030, dated Dec. 9, 2014 (12 pages).
International Preliminary Report on Patentability Chapter I issued in the corresponding PCT International Application PCT/EP2014/069030, dated Mar. 15, 2016 (7 pages).
Farah Shady et al., "Crystalline coating of rapamycin onto a stent: Process development and characterization", International Journal of Pharmaceutics, 445, 2013, pp. 20-28 (9 pages).

* cited by examiner

*Primary Examiner* — Cachet I Proctor
(74) *Attorney, Agent, or Firm* — Adams and Reese LLP; Raymond R. Ferrera

(57) ABSTRACT

The invention relates to a method for coating a vascular endoprosthesis, wherein the outside of the vascular endoprosthesis is wetted at least partially with a first solution of an active substance, the vascular endoprosthesis is moved in a rotational movement about the longitudinal axis of the vascular endoprosthesis, and a radially acting mechanical force is applied to the outside of the vascular endoprosthesis. The rotational movement has the effect that the solution is carried outward by the centrifugal force, such that no active substance deposits in the interior of the vascular endoprosthesis. The application of a mechanical force to the outside of the vascular endoprosthesis then has the effect of creating crystallization nuclei, such that the active substance can crystallize out.

21 Claims, No Drawings

COATING OF A VASCULAR ENDOPROSTHESIS

The invention relates to a method for coating a vascular endoprosthesis. Moreover, the invention relates to the vascular endoprosthesis obtainable by way of the method.

The so-called "minimal invasive techniques" in medicine gain increasingly in significance. For example, in the treatment of vasoconstriction (stenosis), vascular endoprostheses, so-called stents, are inserted into the vessel in order to keep the vessel open. Typically, a vascular endoprosthesis has a tubular shape and is comprised of a braided or lattice structure made of metal or plastic. The vascular endoprosthesis may assume a compressed shape in order to be able to introduce it through a catheter to the target location. At the target location, the endoprosthesis is then dilated to take its expanded shape. Dilatation can be accomplished by means of a balloon. Also known from prior art are auto-expanding vascular endoprostheses which are comprised of a shape memory alloy and which unfold themselves on their own as soon as they are no longer kept in their compressed shape or subjected to a temperature change. The technique of dilating occluded or constricted blood vessels by the aid of a vascular endoprosthesis is also designated as stent angioplasty.

When using conventional vascular endoprostheses, it turned out to be problematic that restenosis often occurs after a certain period of time due to cell proliferation and tissue neogenesis, i.e. the vessel lumen is again constricted. It is tried to prevent this by medicament-coated vascular endoprostheses (so-called drug eluting stents). The medicaments applied may in particular be proliferation inhibitors such as paclitaxel or immunosuppressants such as sirolimus. The coating can be generated by applying the active substance dissolved in a solvent onto the vascular endoprosthesis and then allowing this solvent to evaporate. In this manner, the active substance deposits on the vascular endoprosthesis and is gradually released after its implantation.

Since typical vascular endoprostheses have a braided or lattice structure, and since the circumference of the vascular endoprosthesis thus has a multitude of passages, the wetting of the vascular endoprosthesis with the solvent in which the active substance is dissolved is in general effected both inside and outside. This, however, is not desirable since the active substance on the inside of the vascular endoprosthesis also impedes the embedding of the vascular endoprosthesis into the body's own tissue. Moreover, a crystallization of the active substance on vascular endoprostheses turned out to be difficult. The background resides in that unlike with balloons for balloon angioplasty, the surface of the vascular endoprosthesis is hydrophilic rather than hydrophobic, which is the reason why crystallization nuclei of the typically hydrophobic active substances do not readily form on the surface of the vascular endoprosthesis.

Now, therefore, it is the object to provide a method for coating of vascular endoprostheses that overcomes these problems known from prior art so that in particular the interior of the vascular endoprosthesis remains largely free from the active substance and so that the active substance crystallizes well on the outer surface.

This object is inventively achieved by a method for coating of a vascular endoprosthesis, said method comprising the following steps:
a) at least a partial wetting of the outside of the vascular endoprosthesis with a first solution of an active substance;
b) moving the vascular endoprosthesis into a rotational movement about the longitudinal axis of the vascular endoprosthesis;
c) applying a radially acting mechanical force on the outside of the vascular endoprosthesis.

In a first conventional step (a), the vascular endoprosthesis is wetted with the solution of the active substance. Wetting can be effected in particular by submersion into the solution or by spraying with the solution. In step (b), the vascular endoprosthesis is moved into a fast rotational movement about its longitudinal axis. The occurring centrifugal force takes the effect that the solvent in which the active substance is dissolved is spinned outwardly and the inside of the vascular endoprosthesis remains virtually free from active substance. The vascular endoprosthesis may be in rotation already during step (a), i.e. during wetting with the active substance solution. This is particularly valid if wetting is effected by submersion into the relevant solution. Alternatively, the vascular endoprosthesis can also be moved into rotation only after step (a) has been completed.

In step (c), which chronologically follows steps (a) and (b), by exerting a radially acting mechanical force on the outside of the vascular endoprosthesis, it is assured that crystallization nuclei for the active substance are formed so that the (hydrophobic) active substance crystallizes well on the hydrophilic-surface of the vascular endoprosthesis. For the radially acting force it is of significance that it acts evenly over the entire circumference of the vascular endoprosthesis in those areas where a wetting has occurred. Radial is understood to imply a force that acts from the outside over the circumference, in contrast with an axially acting force that acts on the longitudinal ends of the vascular endoprosthesis.

In particular, a radially acting mechanical force can be exerted by rolling the vascular endoprosthesis over a surface. This surface may be an elastomer surface, for example a rubber surface. The pressure exerted on the vascular endoprosthesis should remain constant so that the application of force on the vascular endoprosthesis is uniform over the entire circumference. When rolling the vascular endoprosthesis over the surface, crystallization nuclei are generated which bear significance for the formation of a crystallized active substance coating. To prevent a deformation of the vascular endoprosthesis when rolling it over a surface, it is purposive to fill-up the interior of the vascular endoprosthesis, for example with a rod inserted in longitudinal direction and preferably made of glass or metal.

As a matter of fact, alternative forms of exerting a radially acting mechanical force are also conceivable. For example, the vascular endoprosthesis can be introduced into an appropriate tool that is suitable for exerting a uniform radially acting mechanical force. The force must be so rated that a non-desirable deformation of the vascular endoprosthesis does not occur.

Regardless of the way of exerting the force, by rolling over a surface or in a different way, a slight pressing-on is typically sufficient, for example with a force of 0.5 to 5 N, preferably 1 to 3 N, e.g. 2 N.

In order to remove the active substance dissolved in a solvent which disadvantageously occurs in the interior of vascular endoprosthesis, the vascular endoprosthesis is moved into a rotational movement about its longitudinal axis. The speed of rotation should at least amount to 1,000 rpm, preferably to at least 2,000 rpm and particularly preferably at least 5,000 rpm. A speed of rotation ranging between 5,000 and 10,000 rpm has turned out to be particular favorable. A correspondingly high rotational speed effectively ensures that the solvent containing the active substance is spinned-off and that the interior area of the vascular endoprosthesis virtually remains free from active substance. Moreover, even remnants of the active substance which span the gaps of the vascular endoprosthesis wholly or partly or which protrude into them are removed. Such active substance remnants are undesirable because it does not constitute a reproducible or quantifiable amount of active substance. Typically, the vascular endoprosthesis is allowed to rotate over a period of 10 s to 12 min after wetting with the first active substance solution, a period of 30 s has turned out to be generally sufficient. The rotational speed is substantially higher than it is with techniques partly known from prior art in which a uniform distribution of the active substance or a drying is intended to be achieved by a movement.

Since the interior of the vascular endoprosthesis remains largely free from active substance. the vascular endoprosthesis is coated faster with endothelium. Stimulation of blood coagulation is equally diminished by the vascular endoprosthesis. By using the inventive vascular endoprostheses, it is therefore possible to more quickly dispense with blood coagulation inhibitors such as acetylsalicylic acid. At the same time, however, restenoses are efficiently prevented by applying the active substance on the outside of the vascular endoprosthesis.

In terms of the active substance, the first solution may be saturated. Eligible for use as solvent, for example, are methylene chloride, chloroform, an alcohol, in particular ethanol, methanol or isopropanol, acetone, diethyl ether, liquid hydrocarbons, such as for example pentane, hexane, heptane, hexanaphthene or octane, toluene, tetrahydrofuran (THF), dimethyl sulfoxide (DMSO), dioxane, dimethylformamide (DMF) or ethyl acetate. A use of solvent blends is also possible. Preferably, it is a solution of the active substance in chloroform or methylene chloride, while preference is given to chloroform because it volatilizes with less speed, thus leaving more time during which the solvent together with the active substance can be spun outwardly by way of the rotational movement.

A typical concentration for the active substance in the first solution lies in a range of 50-500 mg/ml, particularly 100 to 300 mg/ml. These concentrations proved effectiveness in the formation of a paclitaxel coating. In principle, it may also be a saturated active substance solution.

The active substance applied is particularly a pharmaceutical and/or medicament which takes a proliferation-inhibiting effect and which prevents the vessel-constricting overgrow of the spot held open by the vascular endoprosthesis. In particular, the active substance may be chosen from: tretinoin, orphanreceptoragonists, elafin derivates, corticosteroids, steroid hormones, paclitaxel, rapamycin, sirolimus, tacrolimus, hydrophobic proteins as well as cell proliferation changing substances. It is also possible to use blends of these active substances. Moreover, even derivates of the mentioned active substances can be usable, the term derivates meaning in particular salts, esters and amides. Possible for use as steroid hormones are, for example, methylprednisolone, dexamethasone or oestradiol. Especially preferred is the use of paclitaxel and/or paclitaxel derivates.

Coating of the vascular endoprosthesis with the active substance can also be effected by using solubilizers. Known as such are for example: phosphatidylcholine, polyethoxylated castor oil, cardiolipin, cholesterol as well as blends hereof. Preference, however, is given to a waiver of solubilizers.

The afore-mentioned methodical steps, in particular steps (a) and (b) can also be repeated, if required, i.e. an active substance dissolved in a solvent can be applied on the vascular endoprosthesis several times and the interior of the vascular endoprosthesis ca be removed by moving it into a rotational movement. This leads to an increased loading with the active substance. It is also conceivable to apply different active substances consecutively.

In accordance with a particularly preferred embodiment, a process step (d) is taken following the afore-mentioned steps (a) to (c), in which those areas of the outside of the vascular endoprosthesis that have been wetted with the first solution of the active substance are wetted with water and/or with a liquid containing at least one alcohol. This step should be executed after the vascular endoprosthesis has been dried completely or largely and after the active substance has crystallized-out, if possible. The active substance layer thus obtained after wetting the surface with the first solution of the active substance is rather lacquer-like and transparent and serves as a basis for a homogeneous and reproducible active substance loading. Wetting with water and/or a liquid containing at least one alcohol partially attacks the active substance surface and makes it more porous. Thus the coating becomes more brittle, optically less transparent and more milky. Owing to the chalk-like consistency of the surface, a higher active surface abrasion and a higher active surface release to surrounding vessel walls is achieved than it would be the case without wetting with the additional liquid containing water and/or at least one alcohol.

The liquid containing water and/or at least one alcohol is in particular an aqueous hydrous solution containing one alcohol and/or one ketone. The concentration of alcohol and/or ketone in the aqueous solution typically amounts to 10 to 70% (v/v), preferably 20 to 40% (v/v), and particularly preferably to approx. 30% (v/v). Usable in principle are alcohols and ketones mixable with water, while it is also possible to use a mix of several alcohols and/or ketones, which are then subject to those preferred concentration data mentioned hereinabove. Preference is given to the use of ethanol, methanol, acetone, and/or isopropanol. Most preference is given to ethanol. Furthermore, the aqueous solution may comprise an azeotropic solvent mixture, in particular an alcohol/water mixture, giving preference to an ethanol/water mixture. Also possible is the addition of a small quantity, typically approx. 0.1% (v/v), of acetic acid, whereby a stabilization of the active substance, in particular of paclitaxel, is achieved. Wetting with the liquid containing water and/or at least one alcohol is also typically effected by submersion or spraying. After and/or during wetting, the vascular endoprosthesis, in turn, can be moved into rotation and/or be in rotation in order to achieve a faster removal of surplus solvent and to achieve a drying. It is also conceivable that the liquid contains an additional amount of active substance in order to further increase the loading of the vascular endoprosthesis.

As a further step (e) after the afore-mentioned step (d), those vascular endoprosthesis outside areas wetted with the first solution and the liquid containing water and/or at least one alcohol can be wetted with a further solution that contains a polysaccharide. Accordingly, the vascular endoprosthesis is coated on the outside with a polysaccharide, i.e. the active substance is largely covered by a polysaccharide layer. If required, the vascular endoprosthesis can still be liberated from the polysaccharide coating by simple wiping-off, because the polysaccharide does not perform any function here. However, a removal of polysaccharide is not necessarily required, because by way of the methodical step (b) described hereinabove, sufficient care has already been taken to assure that the interior of the vascular endoprosthesis remains virtually free from active substance.

It has become evident that the polysaccharide coating takes an effect similar to that of an adhesive substance on the interior wall of the treated vessel, i.e. the active substance adheres far better to the vessel wall and is less easily entrained by the bloodstream. Presumably, the polysaccharide which in contrast with the active substance is hydrophilic swells-up slightly in an aqueous solution like blood, whereby a transfer to the vessel interior wall is improved. Accordingly, the active substance can unfold its effect over a long period of time and penetrate from the polysaccharide coating gradually into the vessel tissue. It could be demonstrated that significant active substance concentrations are still detectable even after approx. 3 months. Conversely, without a polysaccharide coating, hardly any active substance is still existing in the area of the vessel interior wall after 2 to 3 days, which is why the protection from a restenosis caused by the active substance is no longer given with conventional active-substance coated stents already after a comparably short period of time.

Another advantage of the coating with a polysaccharide should be seen in that the active substance is better fixed to the vascular endoprosthesis. Active substances, e.g. paclitaxel, which are used for a coating of vascular endoprostheses and which take a proliferation-inhibiting effect are often highly toxic, which is the reason why physicians and medical staff have to be protected from inhalation or contact with it. By covering the active substance with a polysaccharide layer, it is achieved that the vascular endoprosthesis can be handled unproblematically without a detaching of the active substance. The risk that a user inhales the active substance or absorbs it through the skin is minimized.

As initially the active substance and then the polysaccharide as a polymer are each applied in dissolved form, a uniform distribution of the polysaccharide around the active substance crystals of the already existing active substance coating is achieved. Moreover, cavities between active substance particles and/or between the surface of the vascular endoprosthesis are filled-up; the active substance crystals are coated and sheathed with the polysaccharide.

In this context, it is of special advantage that the vascular endoprosthesis coating thus obtained is mechanically stable and flexible which is of importance to the extent that a vascular endoprosthesis must often be brought by a catheter through narrow-lumened blood vessels of the point of destination. Packaging and handling of the vascular endoprosthesis, too, becomes correspondingly safer.

Polysaccharides represent a hydrophilic coating which experiences a certain swelling and/or softeninig in an aqueous environment such as blood. As a result hereof, the active substance is well transferred to the interior wall of the vessel during the dilatation of the vascular endoprosthesis. The inventive method is particularly suitable for lipophilic active-substance coatings. For it has become evident that especially hydrophilic polysaccharides are well suitable for assuring that lipophilic active substances are effectively transferred to the inner walls of treated vessels during dilatation and cause a long-lasting active-substance concentration. It is presumed that after the liquid containing water and/or at least one alcohol has effected an embrittlement of the active-substance coating according to the inventive method, the subsequently applied polysaccharide molecules sediment between the active-substance molecules and thus effect a homogeneous distribution of the active substance in the polysaccharide matrix. With vascular endoprostheses manufactured by applying the inventive method, the active substance is advantageously covered by the polysaccharide applied in the final step.

Polysaccharide is preferably available in an alcoholic solution. Apart from one or more alcohol(s), it may especially contain water, too. An aqueous-alcoholic solution is of some advantage to the extent as it dissolves the polysaccharide well, but does not degrade again the active-substance layer already applied. Moreover, the organic portion in the solution effects a rapid drying after wetting. The concentration of the alcohol and/or alcohols in the aqueous-alcoholic solution typically amounts to 10 to 70% (v/v), preferably 30 to 65% (v/v), further preferably 50 to 60% (v/v), and particularly preferably approx. 55% (v/v). Usable as alcohol are those alcohols that dissolve polysaccharide. In general, such alcohols can also be mixed with water. Preference is given to ethanol, methanol, and isopropanol, particularly preferred is ethanol. After and/or already during wetting with a solution containing a polysaccharide, the vascular endoprosthesis, in turn, can be moved in rotation and/or be in rotation in order to remove surplus solution and to effect a quicker drying.

If required, step (d) can also be dispensed with, i.e. methodical step (e) succeeds directly to step (c), because the aqueous-alcoholic solution, in which polysaccharide has already been dissolved, is also suitable to cause the desired embrittlement of the active-substance surface. In this case, step (e) serves a twofold purpose, i.e. on the one hand, the active-substance layer becomes more porous, and on the other hand the active-substance layer is covered with polysaccharide, wherein the polysaccharide also penetrates into the individual cavities and gaps that form in the active-substance layer.

The mean molecular mass of polysaccharide expediently amounts to 10,000 to 100,000,000 Da. A mean molecular mass ranging between 20,000 and 80,000 Da has turned out to be particular expedient. The polysaccharide content of the further solution preferably amounts to 1 to 15 wt. %, further preferably 2 to 10 wt. %, and particularly preferably 3 to 8 wt. %.

The polysaccharide is preferably a branched polysaccharide. Mixtures composed of several polysaccharides and modified polysaccharides are also suitable. Preferred are dextrans, particularly natural dextrans. Dextrans are highly-molecular branched polymers composed of glucose units. Among others, they are produced from bacteria of the *Leuconostoc* species. They are utilized as blood plasma substitutes or as carriers in chromatography. Dextrans additionally have an anti-thrombogenic effect.

The dextran may in particular be a natural dextran. Special preference is given to dextran 40 with a mean molecular mass of approx. 40,000 Da.

However, apart from dextrans, other polysaccharides may in principle be used, too. An example for a usable modified polysaccharide is hydroxethyl starch (HES).

All wettings of the surface of the vascular endoprosthesis with a liquid (first solution, a liquid containing water and/or at least one alcohol or a further solution containing polysaccharide) can be effected by submersion into the liquid. As a rule, submersion takes max. 1 min, typically 10 to 30 sec. As an alternative to a wetting by submersion, the wetting can also be effected in a different way, e.g.

by spraying or dripping. After the individual steps of wetting, the surface of the endoprosthesis is initially typically allowed to dry before further methodical steps are performed. Drying can be supported by letting a current of air or gas take its effect. Moving the vascular endoprosthesis into rotation also supports the drying process.

If required, the surface of the vascular endoprosthesis can be enhanced by mechanical, chemical or thermal impacts, e.g. by roughening or etching, before applying the active substance. In this manner, the surface attains a coarser structure so that the active-substance loading can be increased. Deepenings thus produced in the surface may have a depth and a diameter of 5-50 µm, for example.

All methodical steps can be performed at room temperature.

Apart from the described inventive method, the invention also relates to a vascular endoprosthesis, the outside of which has at least partly a coating with an active substance and which is obtainable by way of the method described hereinabove. The coating with the active substance as well as with the polysaccharide may accordingly relate to the entire outer surface of the vascular endoprosthesis or merely to partial areas. It is of significance that the interior of the vascular endoprosthesis remains as far as possible free from active substance in order to enable endothelium growth there which effects an embedding of the vascular endoprosthesis in the vessel. In this manner, the vascular endoprosthesis is quickly integrated in the body tissue , while at the same time the active substance existing on the outer surface of the vascular endoprosthesis efficiently prevents restenoses due to uncontrolled cell growth The inventive vascular endoprosthesis may for example be a stent which is conventionally known for keeping a vessel lumen open.

It is of special advantage if the active substance is moreover covered by a polysaccharide, particularly by a dextran. The polysaccharide causes a good adhesion of the active substance to the vessel interior wall, so that a carry-over of the active substance by the blood stream is largely prevented. Accordingly, substantial active-substance concentrations are detectable on the vessel interior wall even after months, while with conventional active-substance coated vascular endoprostheses, hardly any active substance is existing on the vessel interior wall partly already after a few days.

The invention claimed is:

1. A method for coating a vascular endoprosthesis, said method comprising the following steps:
    a) at least a partial wetting of the outside of the vascular endoprosthesis with a first solution of an active substance;
    b) moving the vascular endoprosthesis into a rotational movement about the longitudinal axis of the vascular endoprosthesis; and
    c) applying a radially acting mechanical force on the outside of the vascular endoprosthesis, wherein step (b) is executed after step (a) and step (c) is executed after step (b).

2. The method according to claim 1, further comprising; applying the radially acting mechanical force to the outside of the vascular endoprosthesis by rolling the vascular endoprosthesis over a surface by exerting a pressure.

3. The method according to claim 1 further comprising; moving the vascular endoprosthesis into a rotational movement about the longitudinal axis with a rotational speed of at least 1,000 rpm.

4. The method according to claim 1, further comprising: moving the vascular endoprosthesis into a rotational movement about the longitudinal axis with a rotational speed of at least 2,000 rpm.

5. The method according to claim 1, further comprising: moving the vascular endoprosthesis into a rotational movement about the longitudinal axis with a rotational speed of at least 5,000 rpm.

6. The method according to claim 1, further comprising: at least a partial wetting of the outside of the vascular endoprosthesis with a first solution of an active substance and one or more of a chloroform or a dichloromethane as a solvent.

7. The method according to claim 6, further comprising; wetting the areas of the outside of the vascular endoprosthesis wetted with the first solution of the active substance with a liquid comprising at least one or more of ethanol, methanol, acetone, and isopropanol.

8. The method according to claim 1 further comprising; at least a partial wetting of the outside of the vascular endoprosthesis with a first solution of the active solution chosen from one or more of tretinoin, orphanreceptoragonists, elafin derivates, corticosteroids, steroid hormones, paclitaxel, rapamycin, sirolimus, tacrolimus, hydrophobic proteins and cell proliferation changing substances.

9. A method for coating a vascular endoprosthesis, said method comprising the following steps:
    a) at least a partial wetting of the outside of the vascular endoprosthesis with a first solution of an active substance;
    b) moving the vascular endoprosthesis into a rotational movement about the longitudinal axis of the vascular endoprosthesis; and
    c) applying a radially acting mechanical force on the outside of the vascular endoprosthesis; and
    d) wetting the areas of the outside of the vascular endoprosthesis wetted with the first solution of the active substance with a liquid comprising one of water and alcohol, wherein step (d) is executed after steps (a) to (c).

10. The method according to claim 9 further comprising; wetting the areas of the outside of the vascular endoprosthesis wetted with the first solution of the active substance with a liquid comprising at least one of water, alcohol and a ketone.

11. The method according to claim 10, further comprising; wetting the areas of the outside of the vascular endoprosthesis wetted with the first solution of the active substance with a liquid comprising one or more of water, alcohol and a ketone, liquid amounts between 10 up to 70% (v/v).

12. The method according to claim 10, further comprising; wetting the areas of the outside of the vascular endoprosthesis wetted with the first solution of the active substance with a liquid comprising one or more of water, alcohol and a ketone, in liquid amounts between 20 to 40% (v/v).

13. The method according to claim 9, further comprising:
    e) wetting the areas of the outside of the vascular endoprosthesis wetted with the first solution with a liquid comprising one or more of water, alcohol and a further solution that comprises a polysaccharide, wherein step (e) is executed after steps (a) to (d).

14. A method for coating a vascular endoprosthesis, said method comprising the following steps:
    a) at least a partial wetting of the outside of the vascular endoprosthesis with a first solution of an active substance;

b) moving the vascular endoprosthesis into a rotational movement about the longitudinal axis of the vascular endoprosthesis;

c) applying a radially acting mechanical force on the outside of the vascular endoprosthesis; and e) wetting the areas of the outside of the vascular endoprosthesis wetted with the first solution with a liquid comprising one or more of water, alcohol and a further solution that comprises a polysaccharide, wherein step (e) is executed after steps (a) to (c).

15. The method according to claim 14, further comprising;

wetting the areas of the outside of the vascular endoprosthesis wetted with the first solution with a liquid comprising one or more of water, alcohol and a further solution comprising a polysaccharide having a mean molecular mass between 10,000 and 100,000,000 Da.

16. The method according to claim 14, further comprising;

wetting the areas of the outside of the vascular endoprosthesis wetted with the first solution with a liquid comprising one or more of water, alcohol and a further solution comprising a polysaccharide having a mean molecular mass between 20,000 and 80,000 Da.

17. The method according to claim 14 further comprising;

wetting the areas of the outside of the vascular endoprosthesis wetted with the first solution with a liquid comprising one or more of water, alcohol and a further solution comprising a polysaccharide.

18. The method according to claim 17, further comprising;

wetting the areas of the outside of the vascular endoprosthesis wetted with the first solution with a liquid comprising one or more of water, alcohol and a further solution comprising a dextran.

19. A vascular endoprosthesis, comprising an outside portion that is at least partially coated with an active substance obtained from a partially wet first solution of an active substance, wherein the vascular endoprosthesis has been moved into a rotational movement about the longitudinal axis of the vascular endoprosthesis, and a radially acting mechanical force has been applied on the outside of the vascular endoprosthesis according to claim 1.

20. A vascular endoprosthesis according to claim 19, wherein the active substance is covered by a polysaccharide.

21. A vascular endoprosthesis, comprising an outside portion that is at least partially coated with an active substance obtained from a first solution of an active substance, wherein the vascular endoprosthesis has been moved into a rotational movement about the longitudinal axis of the vascular endoprosthesis, and a radially acting mechanical force has been applied on the outside of the vascular endoprosthesis according to claim 1, wherein the areas of the outside of the vascular endoprosthesis wetted with the first solution of the active substance have been wetted with a liquid comprising one of water and alcohol.

* * * * *